(12) United States Patent
Courtright

(10) Patent No.: US 8,733,284 B2
(45) Date of Patent: May 27, 2014

(54) METHOD AND APPARATUS FOR BREEDING FLYING INSECTS

(75) Inventor: Glen Neil Courtright, Yellow Springs, OH (US)

(73) Assignee: Enviroflight, LLC, Yellow Springs, OH (US)

( * ) Notice: Subject to any disclaimer, the term of this patent is extended or adjusted under 35 U.S.C. 154(b) by 153 days.

(21) Appl. No.: 13/551,918

(22) Filed: Jul. 18, 2012

(65) Prior Publication Data

US 2014/0020630 A1    Jan. 23, 2014

(51) Int. Cl.
   *A01K 29/00* (2006.01)
(52) U.S. Cl.
   CPC ...................... *A01K 29/00* (2013.01)
   USPC ......................................................... 119/6.6
(58) Field of Classification Search
   CPC ...................................................... A01K 29/00
   USPC ........................................ 119/6.5, 6.6, 417
   See application file for complete search history.

(56) References Cited

U.S. PATENT DOCUMENTS

| 3,653,357 | A | * | 4/1972 | Sheidlower et al. | 119/6.5 |
| 3,893,420 | A | * | 7/1975 | Andreev et al. | 119/6.6 |
| 4,850,305 | A | * | 7/1989 | Georgi et al. | 119/6.6 |
| D347,913 | S | * | 6/1994 | Wellington et al. | D30/108 |
| 6,223,690 | B1 | * | 5/2001 | Park | 119/248 |
| 2010/0101501 | A1 | * | 4/2010 | Mcpherson | 119/436 |

* cited by examiner

Primary Examiner — Monica Williams
(74) Attorney, Agent, or Firm — Thompson Hine L.L.P.

(57) ABSTRACT

The invention relates to a method and apparatus for breeding flying insects, more particularly flies, and still more particularly black soldier flies. An apparatus for the production and collection of flying insect eggs comprising: a vessel for containing a substrate upon which larvae and/or pupae develop into flying insects, a cage for retaining the insects, a tubular passage or duct connecting the vessel to the cage through which the flies travel from the vessel to the cage, a moist substrate within the cage upon which the insects will lay eggs, and a light source within or proximate the cage for providing light of a wavelength that enhances the tendency of the insects in the cage to mate.

14 Claims, 4 Drawing Sheets

METHOD AND APPARATUS FOR BREEDING FLYING INSECTS

FIELD

The invention relates to a method and apparatus for breeding flying insects, more particularly flies, and still more particularly black soldier flies. The insects can be used as animal feed or used to breed larvae and pupae that are useful as an animal feed. Alternatively, the insects are used in an insect-based process for converting cereal byproducts such as dried distiller grain with solubles (DDGS), modified wet cake, and spent brewers grains to a high value feeds and natural oils for use in aquaculture diets and other agriculture feed products.

SUMMARY

The invention provides a method and an apparatus that is useful in breeding flying insects. In related U.S. application Ser. No. 13/551,909 filed on even date herewith, which is herein incorporated by reference, an insect-based bioconversion process and reactor are described which are useful in transforming cereal byproducts such as dried distiller grain with solubles (DDGS), modified wet cake, and spent brewers grains into high value feeds and oils. Certain embodiments of the process are designed for installation adjacent to distilleries, breweries, and ethanol plants to convert the cereal byproducts of the fermentation and distillation process into high value, high protein feeds and natural oils. The aquaculture industry is constrained by the availability of cost-effective quality feeds. By subjecting the byproducts to insect based bioconversion, the byproducts are converted to a protein source that closely resembles fish meal for use in aquaculture diets for species such as trout, salmon, yellow perch, marine shrimp, tilapia, basa, freshwater prawn, minnows, and crayfish. In fact the process yields two primary products, namely: (1) an animal-based high protein meal obtained from the insect larvae; and (2) low fat, plant based proteins obtained from the insect waste stream known as frass which can contain a natural attractant making it particularly palatable to fish. In another embodiment of that invention, an oil product is obtained which may be useful in producing animal feed supplements and oleochemicals. The oil product is derived from the insect bodies and is high in lauric acid which is beneficial to the health of animals such as swine, ruminants, and reptiles.

It has been found that the black soldier fly ((*Hermetic illucens*) larvae is able to convert low brewery and distillery byproducts into aquaculture feeds. The black soldier fly is an insect native to North America. It has been reported that the fly does not spread disease or pathogens because the adult fly lives only a short time and does not feed during its short life (as contrasted with house flies which spread disease and other pathogens).

In accordance with one embodiment, an apparatus for the production and collection of flying insect eggs is provided which comprises:

an opaque vessel filled with a mixture of insect pupae and high permeability/low water retention substrate (such as perlite or vermiculite) where insect pupae develop into flies,
a cage for retaining the flies,
a tubular passage connecting the vessel to the cage through which the insects travel from the vessel to the cage,
a moist substrate within the cage upon which the insects will hydrate and deposit eggs,
an artificial light source within or proximate to the cage of a wavelength and intensity that is useful for enhancing or eliciting mating behavior, for example, during low sunlight conditions.

In accordance with one embodiment of the invention, the apparatus includes a source of forced air which may be temperature and humidity adjusted and is directed into the vessel and out of the passageway connecting the vessel to the cage.

In accordance with an another embodiment of the invention, a source of water is provided which dispenses water onto the substrate in the cage. That substrate may be a sponge.

In another embodiment of the invention, the cage includes a floor that is vibrated. The floor may be vibrated by a transducer and, in one embodiment, the transducer is a low frequency audio speaker.

The light source is a quartz halogen lamp and, more particularly, a quartz halogen bromine lamp. The light source may be used in conjunction with a sensor which controls the light source such that the light is turned on when it is desired to supplement the ambient sunlight and increase the frequency with which the insects mate.

In a further embodiment of the invention, the floor of the cage is sloped or parabolic shaped and has an opening at the focal point of the floor which is fitted with a removable container for collecting dead insects.

Another manifestation of the invention is a method for producing flying insect eggs which comprises:

an opaque vessel filled with a mixture of insect pupae and high permeability/low water retention substrate (such as perlite or vermiculite) where insect pupae develop into flies,
forcing air through a translucent or transparent tubular passage between the vessel and the cage to cause the insects to travel into the cage,
placing a moist substrate in the cage upon which the insects lay eggs,
removing the insect eggs from the cage, and
removing dead insects from the cage.

DETAILED DESCRIPTION OF THE INVENTION

Figure 1:
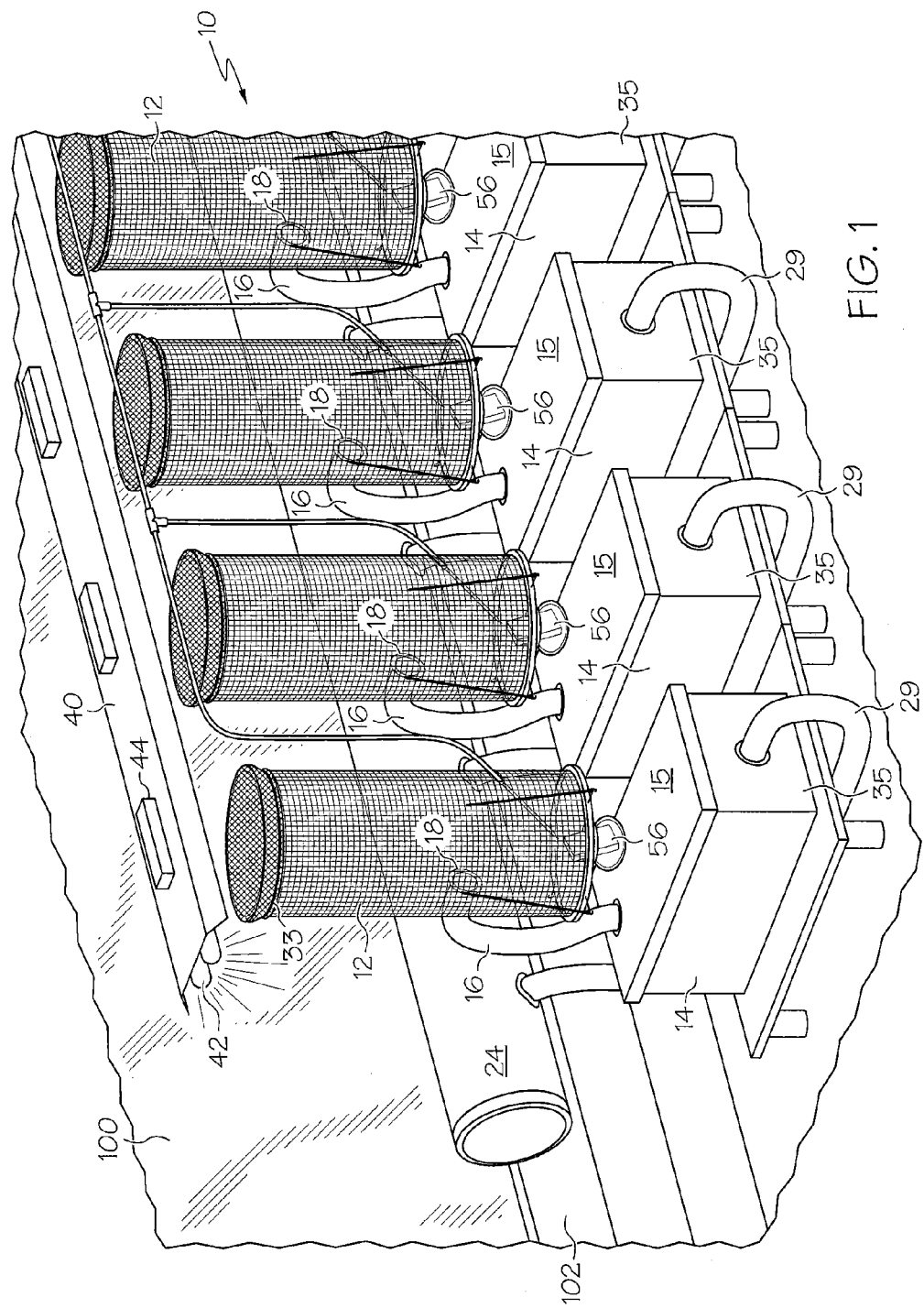
FIG. 1 illustrates an apparatus for breeding flying insects in accordance with one embodiment of the invention.
Figure 2:
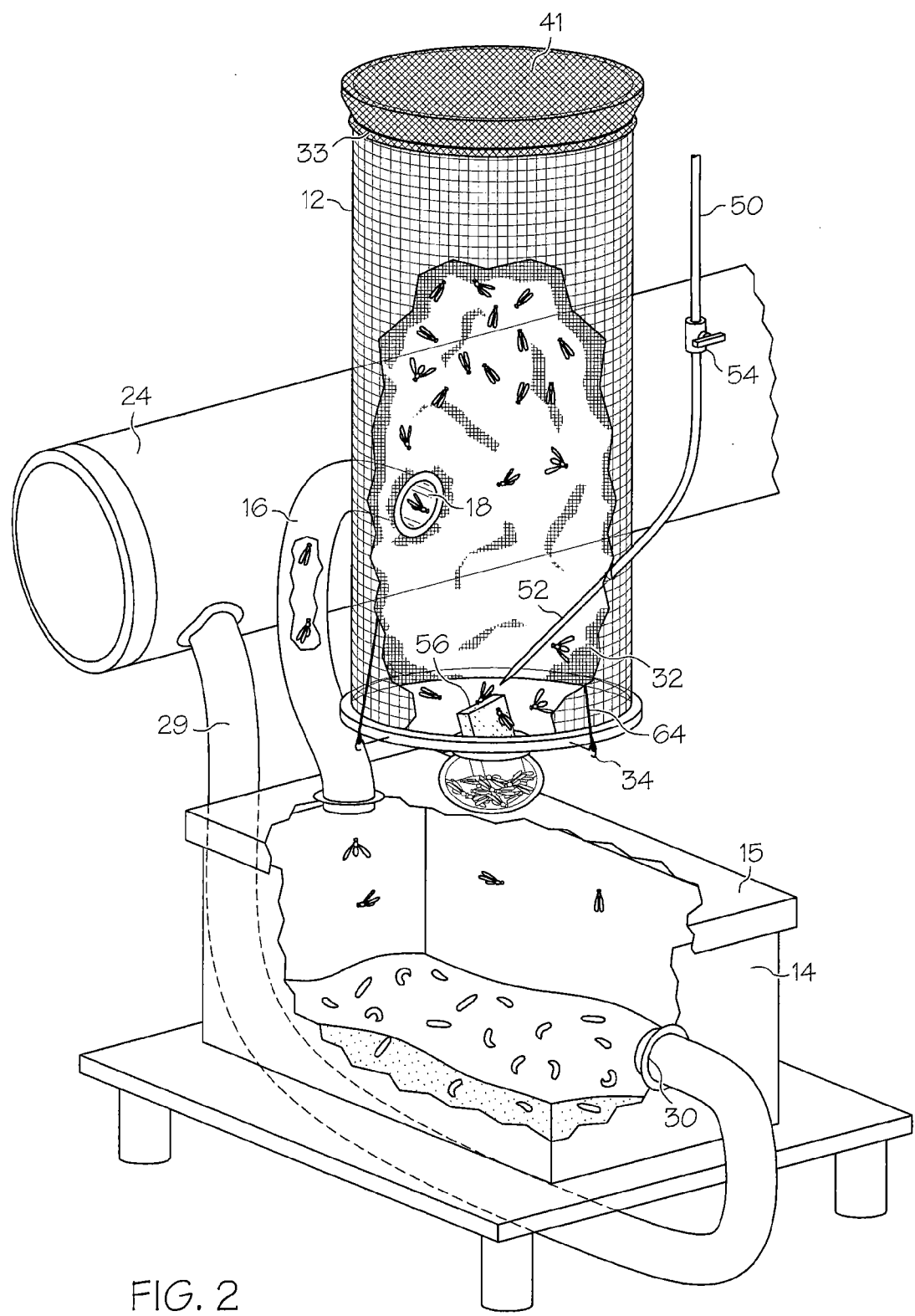
FIG. 2 illustrates a cage in accordance with one embodiment of the invention.
Figure 3:
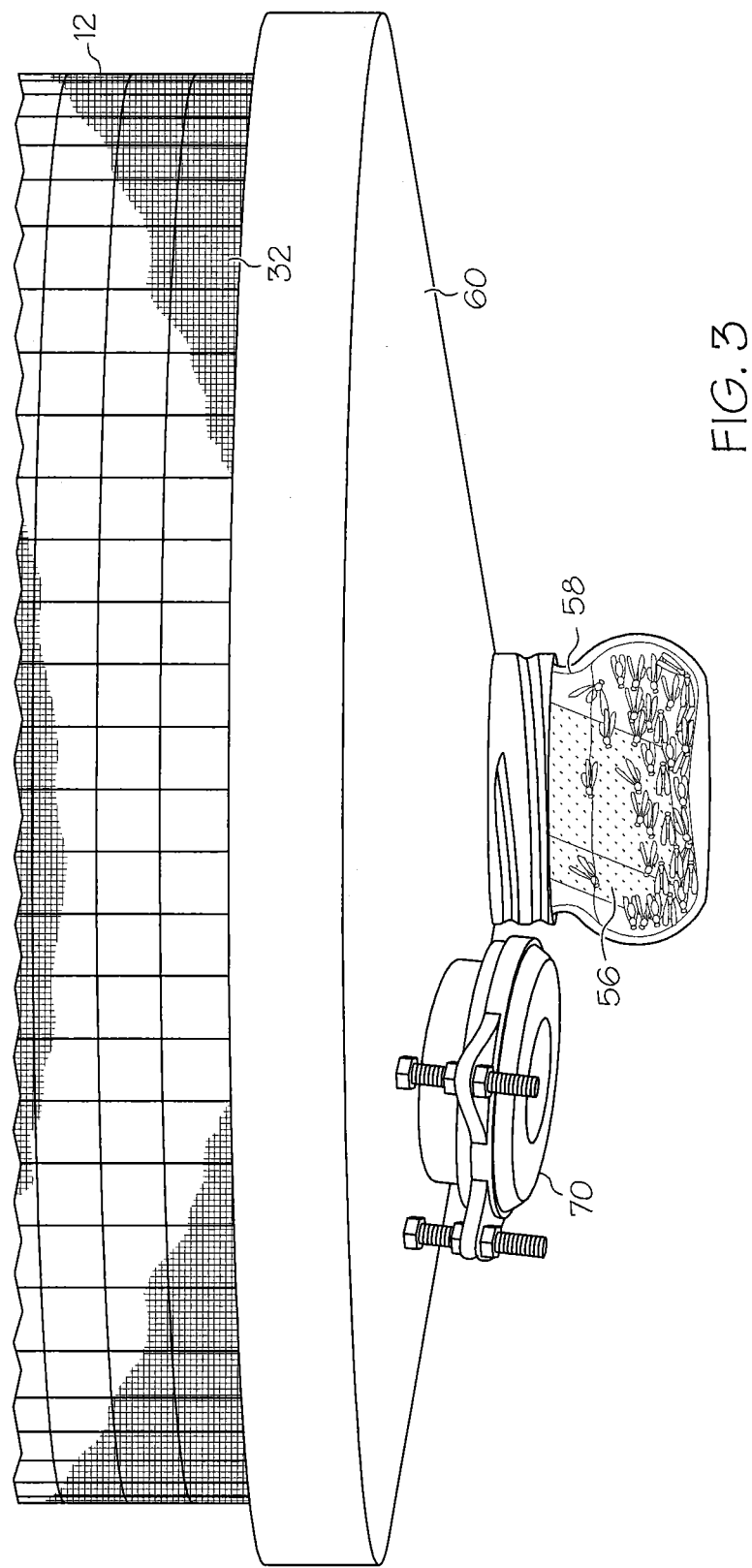
FIG. 3 is an enlarged view of the floor of a cage including a transducer for vibrating the floor in accordance with one embodiment of the invention.

FIG. 1 illustrates one embodiment of an apparatus 10 in accordance with the invention. The apparatus 10 includes at least one but typically multiple cages 12 and at least one covered bin 14. The bin contains a substrate (such as a high permeability/low water retention substrate such as perlite or vermiculite) where insect pupae develop into flies. The apparatus 10 is particularly useful in raising flies and, still more particularly, black soldier flies. Hereinafter, the invention will be described with respect to breeding or developing black soldier flies but it should be understood that the apparatus can be used to raise a variety of flying insects and flies in particular. In accordance with one embodiment, the apparatus is housed within a greenhouse.

In the illustrated embodiment, a duct or tubular passage 16 is provided over an opening in the top 15 of the bin 14. A flexible, transparent or translucent venting tube may be used to attract the insects to the passage and hence into the cage. The passage connects to an opening 18 in the side 20 of the cage 12. An air duct 24 directs air from a blower 26. In one embodiment the air is at a temperature of about 24 to 36° C. and may be humidified to a relative humidity of about 40 to 50% at 30° C. The air supply duct 24 includes a smaller duct 29 which directs air through an opening 30 in the side wall 35 of the bin 12 at an air flow rate of about 125 cu. ft./min. The apparatus 10 may be housed within a greenhouse 100 in accordance with one embodiment of the invention. In the illustrated embodiment, the lower portion 102 of the walls of the greenhouse 100 are constructed of a material, such as wood, which shades the bin(s) 12 from direct sunlight. The upper portions of the greenhouse walls 102 may be formed from glass or a light transmitting plastic conventionally used in greenhouse construction. In accordance with one embodiment, the greenhouse is maintained at a temperature about 30° C.

Figure 4:
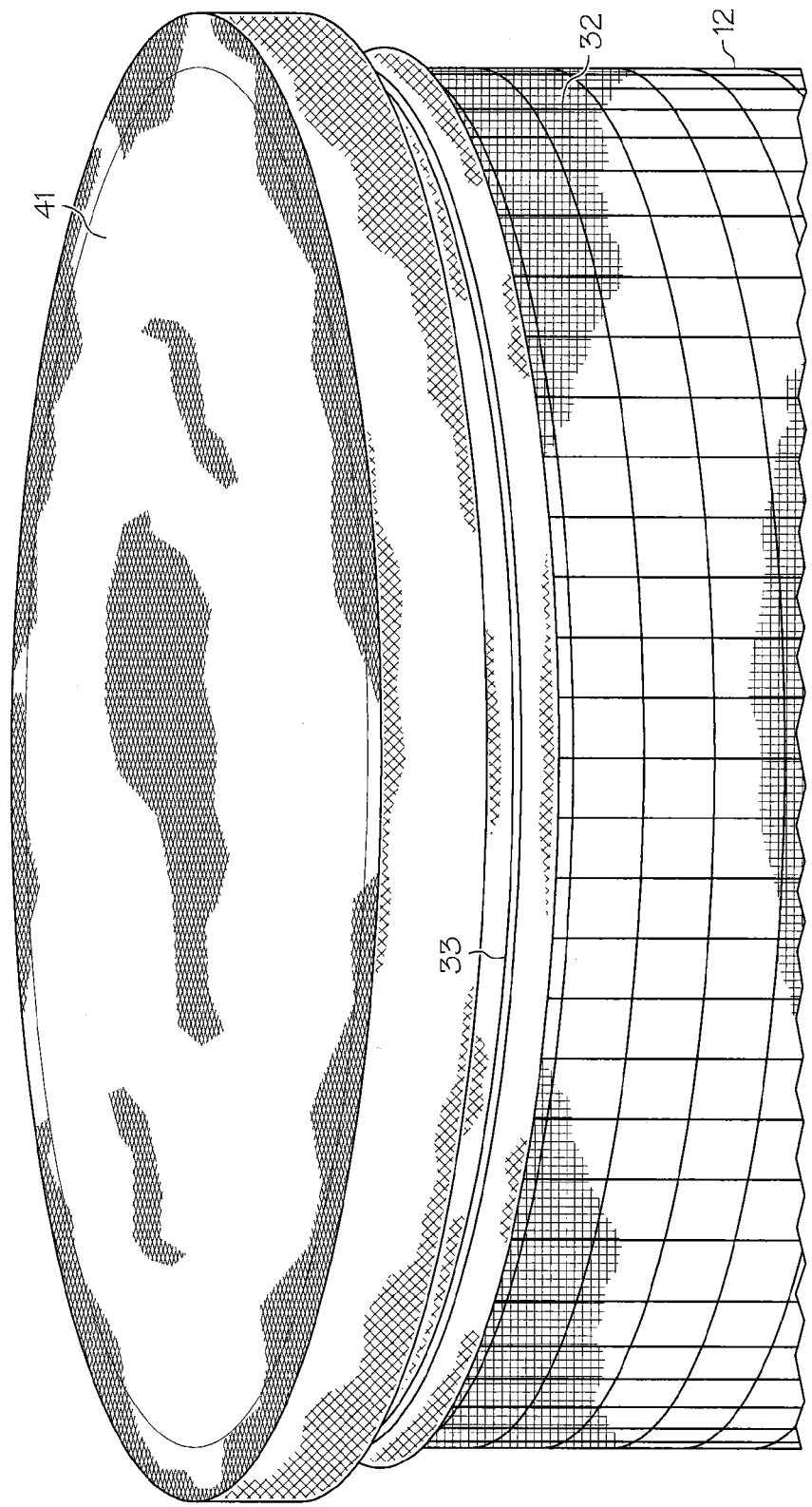
FIG. 4 is an enlarged view of the top of the cage.

The cage 12 is circular. The use of a circular tubular cage is desirable because the black flies tend to fly in a circular path. However, cages having a noncircular cross section are not precluded. The illustrated cage is formed from a tubular wire mesh material that is lined with a smaller mesh screen 32. The screen 32 has a small enough mesh to keep the flies from escaping and is secured to the wire fence 30. At the top of the cage, the screen is secured with a plastic or metal band 33 as shown in FIG. 4. At the top 41 of the cage, a reflector 40 which may be aluminum sheet metal and a light source 42 are provided. While it is natural to provide the light source at the top of the cage, other locations are also suitable. The light source may be a quartz halogen lamp filled with bromine gas. This lamp emits light in a spectra which is often filtered by cloud cover. The lamp 42 is connected to a sensor 44 which turns the lamp on or off depending upon the ambient light conditions in the cage. It has been found that the black soldier fly mates more frequently in full sunlight and less frequently on cloudy days. It has been found that this mating tendency is a function of the availability of full spectrum light. Accordingly, on days or at times at which the amount of light at this wavelength within the mating range is below a specified threshold, the lamp 42 is activated. In this way, the production of eggs is less dependent on ambient conditions.

The black soldier fly does not feed, but it does require water during its short lifetime. Water is supplied to the cage through a small hose 50 which passes through the cage wall 20 and is joined to a pipet 52. The hose 50 includes a valve 54 for adjusting the water flow so that it drips onto the sponge 56 in the cage. The sponge sits in a well 58 on the floor 60 at the bottom of the cage. It is desirable to design the bottom of the cage so that it can be easily removed and cleaned. In one embodiment the bottom of the cage includes a plurality of hooks or eyelets 34 which are connected to elastic cords 64 that are hooked to the wall 20 of the cages.

The floor 60 of the cage may be a non-rusting metal, such as aluminum or stainless steel, or certain rigid plastics may be used. A transducer 70 is mounted to the outside surface of the floor 60 of the cage 12 in order to cause the floor to vibrate as the flies mate and lay eggs. The vibration assists in cleaning the cage and collecting the eggs by causing dead flies and eggs to slide down the floor and into the well 58. A container or glass jar having a threaded neck may be screwed into the opening. The jar collects the dead flies.

The apparatus 10 typically contain multiple cages. In the illustrated embodiment eight cages are provided on each side of the greenhouse containing the apparatus. The larvae-fly life cycle is approximately ten days after which it is usually desirable to remove the dead flies and to replace the substrate and empty pupae casings in the bin 14 with a fresh batch. The sponge is removed daily to collect the eggs and replaced with a fresh sponge. By using multiple cages, the development of the flies can be staged so that a source of eggs is available for use as they are required.

Having described the invention in detail and by reference to specific embodiments thereof, it will be apparent that numerous modifications and variations are possible without departing the spirit and scope of the following claims.

What is claimed is:

1. An apparatus for the production and collection of flying insect eggs comprising:
    an opaque vessel filled with a mixture of insect pupae and a substrate where insect pupae develop into flies,
    a cage for retaining the insects,
    a tubular passage between the vessel and the cage to cause the insects to travel into the cage,
    a moist substrate in the cage upon which the insects lay eggs, and
    a light source within or proximate the cage for providing light of a wavelength that elicits or enhances the tendency of the insects in the cage to mate,
    a source of forced air directed into the vessel and from the vessel into the passage, and
    wherein the apparatus includes a supply of water that dispenses water onto the substrate.

2. The apparatus of claim 1 wherein the moist substrate is a sponge.

3. The apparatus of claim 1 wherein the cage includes a floor that is vibrated.

4. The apparatus of claim 3 wherein the floor is vibrated by a transducer.

5. The apparatus of claim 4 wherein the transducer is an audio speaker.

6. The apparatus of claim 1 wherein the light source is a quartz halogen lamp.

7. The apparatus of claim 6 wherein the halogen is bromine.

8. The apparatus of claim 7 additionally including a light sensor which is electronically connected to the light source such that the light source is activated when conditions in the cage require it.

9. The apparatus of claim 1 wherein the cage includes a floor, the floor is sloped or parabolic and has an aperture therein and the aperture is fitted with a container for collecting eggs and/or dead insects.

10. The apparatus of claim 1 wherein the substrate is perlite or vermiculite.

11. The apparatus of claim 1 wherein the tubular passage is transparent or translucent.

12. A method for producing flying insect eggs which comprises
    providing an opaque vessel filled with a mixture of insect pupae and a substrate where insect pupae develop into flies,
    forcing air through a transparent or translucent tubular passage between the vessel and a cage to cause the insects to travel from the vessel and into the cage,
    placing a moist substrate in the cage upon which the insects lay eggs,
    removing the insect eggs and dead insects from the cage, and
    wherein the insects are black soldier flies.

13. The method of claim 12 wherein the method includes activating a light source to enhance the tendency for the insects to mate in the cage.

14. The method of claim 12 wherein the substrate is perlite or vermiculite.

* * * * *

UNITED STATES PATENT AND TRADEMARK OFFICE
CERTIFICATE OF CORRECTION

| | |
|---|---|
| PATENT NO. | : 8,733,284 B2 |
| APPLICATION NO. | : 13/551918 |
| DATED | : May 27, 2014 |
| INVENTOR(S) | : Glen Neil Courtright |

It is certified that error appears in the above-identified patent and that said Letters Patent is hereby corrected as shown below:

On the Title page of the patent:

Item (73) Assignee, reads, "Enviroflight, LLC"

It should read, -- EnviroFlight, LLC --

Signed and Sealed this
Seventh Day of October, 2014

Michelle K. Lee
*Deputy Director of the United States Patent and Trademark Office*